United States Patent
Hansen et al.

(10) Patent No.: US 9,724,227 B2
(45) Date of Patent: Aug. 8, 2017

(54) BASE PLATE FOR AN OSTOMY APPLIANCE

(75) Inventors: Michael Hansen, Gilleleje (DK);
Dorrit Diana Israelson, Gentofte (DK);
Henrik Edvardsen, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 171 days.

(21) Appl. No.: 13/880,056

(22) PCT Filed: Oct. 20, 2011

(86) PCT No.: PCT/DK2011/050397
§ 371 (c)(1),
(2), (4) Date: Apr. 18, 2013

(87) PCT Pub. No.: WO2012/052031
PCT Pub. Date: Apr. 26, 2012

(65) Prior Publication Data
US 2013/0226117 A1    Aug. 29, 2013

(30) Foreign Application Priority Data
Oct. 20, 2010   (DK) .................................. 2010 70445

(51) Int. Cl.
*A61F 5/443* (2006.01)
*A61F 5/448* (2006.01)

(52) U.S. Cl.
CPC .............. *A61F 5/443* (2013.01); *A61F 5/448* (2013.01)

(58) Field of Classification Search
USPC ......................................................... 604/338
See application file for complete search history.

(56) References Cited

U.S. PATENT DOCUMENTS

| | | | |
|---|---|---|---|
| 2,703,576 A | | 3/1955 | Furr, Jr. |
| 4,367,732 A | * | 1/1983 | Poulsen .............. A61L 24/0094 602/56 |
| 4,701,169 A | * | 10/1987 | Steer ...................... A61F 5/443 604/338 |
| 4,892,530 A | * | 1/1990 | Steer ...................... A61F 5/448 604/338 |
| 5,051,259 A | * | 9/1991 | Olsen ..................... A61F 5/445 424/443 |
| 5,486,158 A | * | 1/1996 | Samuelsen ........... A61F 13/025 602/43 |
| 5,714,225 A | * | 2/1998 | Hansen .................. A61F 5/443 424/443 |

(Continued)

FOREIGN PATENT DOCUMENTS

| | | |
|---|---|---|
| EP | 0227317 A1 | 7/1987 |
| EP | 0938349 | 9/2004 |
| WO | 9855057 A1 | 12/1998 |

*Primary Examiner* — Tatyana Zalukaeva
*Assistant Examiner* — Guy K Townsend
(74) *Attorney, Agent, or Firm* — Coloplast Corp., Coloplast A/S; Nick Baumann

(57) ABSTRACT

Disclosed is a base plate 1 for an ostomy collection device, comprising a cover layer 2 whereon an adhesive layer 3 is at least partly disposed. Immediately surrounding a through-going hole 6, the base plate has an inner area wherein the cover layer extends beyond the adhesive layer in a radial direction toward the through-going hole, thereby providing an overlap 7 protecting the adhesive material from contact with stomal output.

13 Claims, 2 Drawing Sheets

(56) References Cited

U.S. PATENT DOCUMENTS

| | | | | |
|---|---|---|---|---|
| 5,811,116 | A | * | 9/1998 | Gilman ............... A61F 5/443 424/443 |
| 5,865,819 | A | * | 2/1999 | Cisko, Jr. ............ A61F 5/445 604/327 |
| 6,071,268 | A | | 6/2000 | Wagner |
| 6,332,879 | B1 | * | 12/2001 | Nielsen ............... A61F 5/443 604/332 |
| 6,589,222 | B1 | * | 7/2003 | Olsen ................. A61F 5/443 604/336 |
| 2004/0193122 | A1 | | 9/2004 | Cline et al. |
| 2004/0260256 | A1 | * | 12/2004 | Ciok .................. A61F 5/445 604/332 |
| 2009/0163883 | A1 | | 6/2009 | Christensen et al. |
| 2009/0312685 | A1 | * | 12/2009 | Olsen ................. A61F 5/443 602/54 |
| 2010/0022933 | A1 | * | 1/2010 | Oelund ............... A61F 5/443 602/54 |
| 2010/0324511 | A1 | * | 12/2010 | Dove et al. ............ 604/342 |
| 2011/0054425 | A1 | * | 3/2011 | Smith ................. A61F 5/448 604/342 |
| 2013/0226117 | A1 | * | 8/2013 | Hansen ............... A61F 5/448 604/338 |

* cited by examiner

BASE PLATE FOR AN OSTOMY APPLIANCE

TECHNICAL FIELD

The present invention relates to an adhesive base plate for use with an ostomy appliance. In particular, the base plate is provided with means for preventing output from the stoma from coming into contact with the peristomal area.

BACKGROUND

It is a common problem for ostomates that the skin area close to stoma, also referred to as the peristomal area, is often irritated and sensitive. This is caused by stomal effluent, i.e. output from the stoma, running back from the stoma opening, along the outer surface of the stoma and into contact with the peristomal skin area.

The output is very aggressive and quickly irritates the skin. Moreover, when the user is wearing a base plate for use in an ostomy device, either a one-piece or a two-piece device, then there is a high risk that the returning output comes into contact with the inner edge of the adhesive of the plate. When in contact with the adhesive, the aggressive output will then erode the adhesive away.

In addition, seeing that sutures may have been used for securing the stoma during surgery or subsequent complications, the peristomal area may be scarred making it even more difficult to provide a seal between the skin and the adhesive wafer. This can create small gaps between the skin and the base plate where the output may enter, thus creating a moist environment that further irritates the skin but also deteriorates the adhesive attachment between the adhesive and the skin resulting in leakage or even dislodging of the base plate.

The present invention solves this problem by providing a protective cover which is able to follow the movement of the stoma while allowing at least a part of the peristomal skin area to be free, thus preventing accumulation of moisture that may further irritate the skin.

BRIEF DESCRIPTION

The description relates to a base plate for an ostomy collection device, the base plate comprising a cover layer whereon an adhesive layer for adhering to the skin is at least partly disposed, a through-going hole extending axially through the base plate, wherein the base plate further comprises an inner area which encircles the through-going hole, and wherein the cover layer extends beyond the adhesive layer in a radial direction toward the through-going hole, thereby providing an overlap.

This provides a base plate where the overlap of the cover layer is not covered by an adhesive prior to use. Such a construction provides a base plate where the overlap provides a protective shield against effluent from the stoma. This reduces the risk of output from the stoma running back on the outside of the stoma and into the through-going hole where it may come into contact with the adhesive layer. Thus, the risk of the adhesive layer being exposed to the aggressive effluent is reduced, thereby increasing the wear time of the base plate.

In one embodiment of the base plate, the adhesive layer comprises at least two different adhesives disposed radially with respect to each other, and wherein the adhesive in the inner area is formed of a soft adhesive.

It should be noted that the soft adhesive does not necessarily have to be moulded snugly against the stoma. The main purpose of the soft adhesive is, however, to provide a seal against the skin. The soft adhesive is able to flow into uneven skin topography of a user. Such uneven topography is often formed by scar tissue and other irregularities.

Alternatively, the soft adhesive may form an outer area, i.e. the radial disposition of the at least two adhesives may be so that a soft adhesive is used in an area radially outside another adhesive type seen in relation to the through-going hole.

A soft adhesive as referred to herein is an adhesive which provides a high flexibility. Such a soft adhesive composition can, for example, be formed of a moisture permeable polymer selected from the group of, but not limited to, polypropyleneoxide, polyurethane, silicone, polyacrylate, ethylene vinyl acetate and mixtures thereof. The cover layer is chosen so that it has a similar flexibility. Thus, a very flexible adhesive wafer is provided, which advantageously easily conforms to the topography of the skin, making it very comfortable to wear.

In one embodiment, at least a part of the cover layer is a backing layer formed of a sheet material, such as a polyurethane film.

In an additional or alternative embodiment, the cover layer in the inner area is a foam. The foam provides a resilient material and has a softness which makes it suitable as a buffer layer between the soft adhesive and the stoma. Moreover, the resilience of the foam will allow it to follow the movement of the stoma, and the softness of the foam will make it comfortable to wear and prevent it from cutting into the stoma.

In embodiments, the foam may be predominantly gas permeable, e.g. an open-celled foam type to allow water vapour to permeate through.

In embodiments, the foam may be a memory-foam such as known from common single-use ear plugs, i.e. such as a polyurethane-based foam comprising additives to increase its viscosity and density. This type is also referred to as visco-elastic PU-foam or low-resilience PU-foam.

In one embodiment, the overlap is between 5 and 15 mm. This places the soft adhesive in a small distance away from the stoma, thereby avoiding the most uneven skin topography, as the area closest to the stoma often has the worst scar tissue as a result from e.g. sutures and frequent contact with effluents.

In order to have a sufficient area to provide an effective seal, the radial extent of the soft adhesive in the inner area is between 4 and 10 mm, preferably 5 mm.

In one embodiment, the adhesive layer in the inner area has swelling properties. Such swelling properties may be provided by adding an absorbent compound to the adhesive, such as hydrocolloid particles.

The swelling properties of the adhesive in the inner layer may thus be used as a sealing mechanism, as the adhesive will press towards and overlap the stoma and even swell into close contact with the stoma.

DETAILED DESCRIPTION

Figure 1:
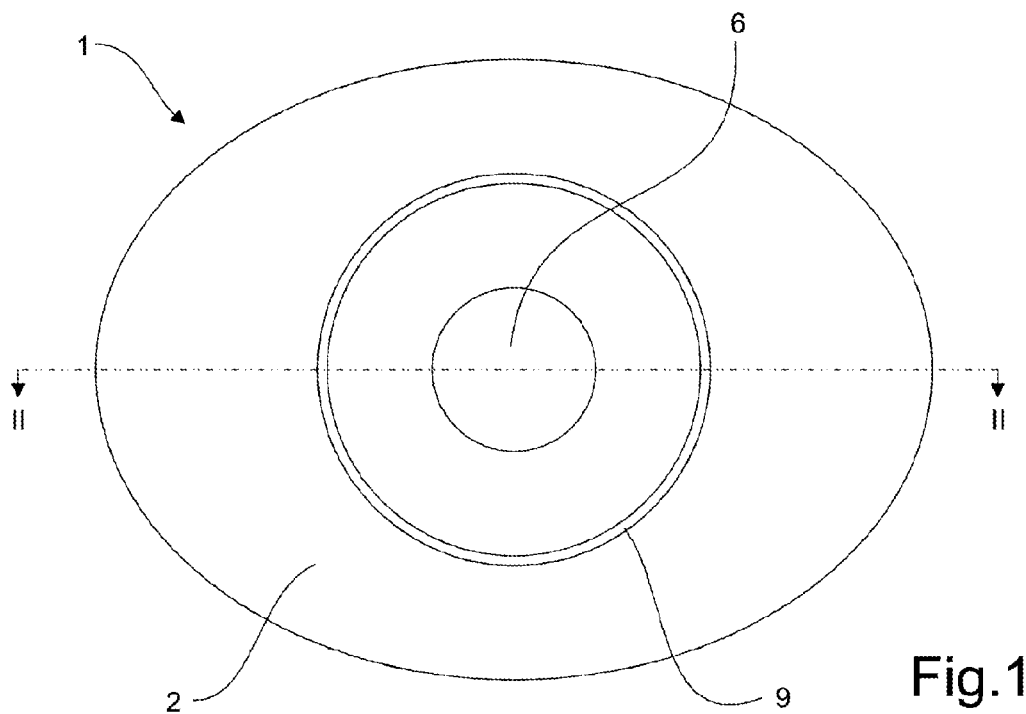
FIG. 1 shows a top view of an embodiment of the invention.
Figure 2:
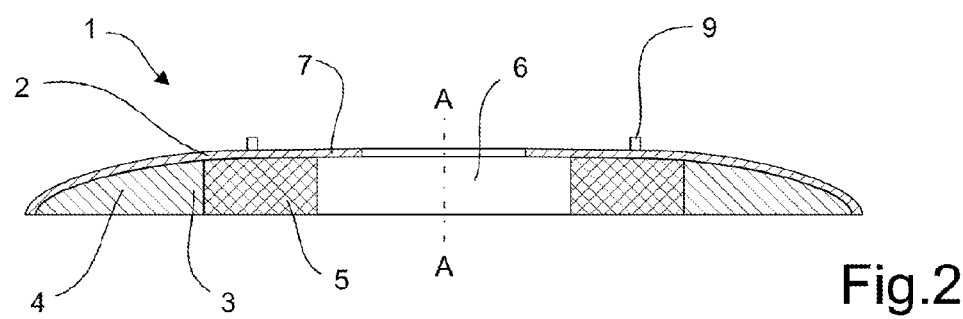
FIG. 2 shows, in section along lines II-II, the embodiment of FIG. 1.

A first embodiment of a base plate 1 is shown in FIGS. 1 and 2. The base plate has a cover layer in the form of a backing layer 2 whereon an adhesive layer 3 has been disposed.

The adhesive layer 3 is in the form of an outer adhesive 4, which is a high tack adhesive, and an inner adhesive 5. The inner adhesive encircles a through-going hole, which extends axially along axis A-A through the base plate. The inner adhesive and the backing layer whereon it is disposed form an inner area defining the through-going hole. The inner adhesive is softer than the outer adhesive, i.e. it will take the shape of the topography of the skin and thus provide a good seal to the skin.

The backing layer 2 extends beyond the adhesive layer 3 in a radial direction toward the through-going hole. This provides an overlap in the shape of an inner flange 7. The flange will function as a seal against the stoma and protect the adhesive layer from stomal output.

A coupling ring 9 is provided to which an ostomy bag may be coupled. However, other coupling solutions, which are well known to the person skilled in the art, may be used without deviating from the scope of the present invention.

Figure 3:
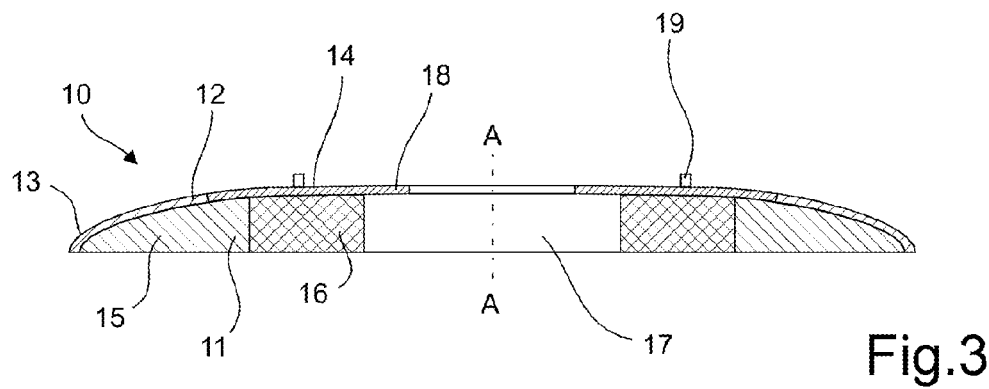
FIG. 3 shows, in section along the same line as in FIG. 2, an alternative embodiment.

A second embodiment of a base plate 10 is shown in FIG. 3. An adhesive layer 11 is disposed on a cover layer 12. The cover layer is formed by an outer backing layer 13 which encircles an inner foam layer 14. The adhesive layer is formed of an outer adhesive 15 which is disposed on the backing layer and an inner adhesive 16 which is disposed on the foam layer. As seen in the figure, there may be a small overlap, i.e. some of the outer adhesive may be arranged on the foam layer or vice versa.

A coupling ring 19 is provided to which an ostomy bag may be coupled. However, other coupling solutions may be used without deviating from the scope of the present invention.

The foam layer and the inner adhesive form an inner area defining a through-going hole 17 which extends axially through the base plate along axis A-A. Similar to the embodiment in FIGS. 1 and 2 the foam layer extends beyond the inner adhesive creating an overlap in the form of a flange 18. Seeing that the flange is formed of a foam it does not only protect the adhesive layer from effluents, but its resilient and soft characteristics makes it suitable as a seal around the stoma as it may follow the movement of the user without cutting or otherwise irritating the stoma during use. Preferably, the foam is a closed cell foam, however, other foams showing resilient characteristics may be used.

Figure 4:
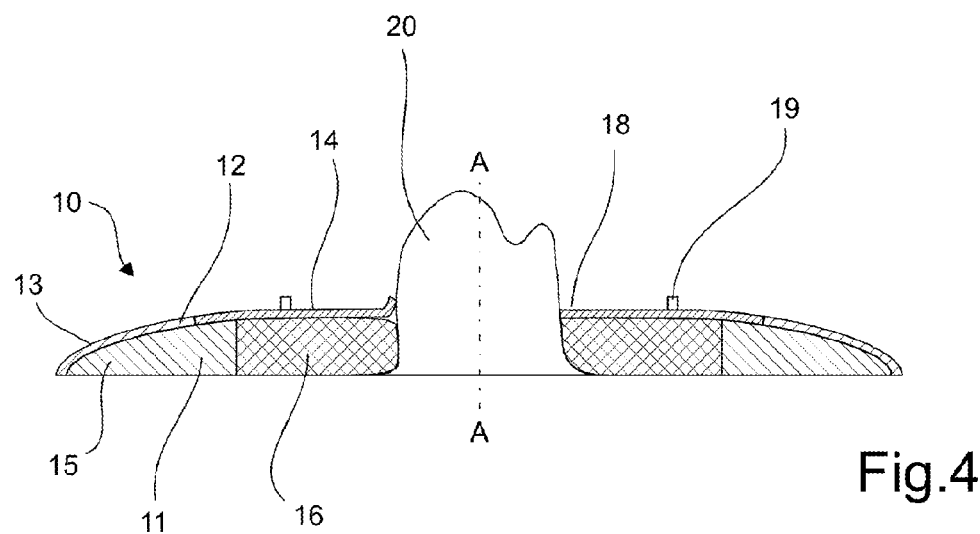
FIG. 4 shows the embodiment of FIG. 3 applied to a user.

FIG. 4 shows the second embodiment of the base plate 10 arranged around a stoma 20. As can be seen the inner adhesive 16 has swollen and provides a seal against the stoma. The inner foam layer 14 conforms to the shape of the stoma and provides an outer barrier preventing stoma effluents from running down the outside of the stoma and into contact with the inner adhesive 16. The inner foam layer also functions as a barrier preventing the inner adhesive from expanding outwardly, i.e. in an axial direction along axis A-A, but only inwardly towards the stoma.

Although it is desired to prevent moisture from contact with the adhesive, it is not possible to completely avoid this as the skin will perspire and release moisture. This is acknowledged in the prior art and has led to the development of hydrocolloid adhesives which will deteriorate over time, however, at a much slower pace than if stomal effluents were to get in contact with the adhesive.

However, by using this knowledge in the invention, it was realized that the swelling of the inner adhesive would aid in sealing around the stoma as the swelling adhesive presses the overlapping flange 18 towards the stoma. At the same time, the foam layer provides a physical barrier that controls the swelling of the adhesive and keeps it in place while it is swollen and has reduced coherent strength. Thus, a faster swelling inner adhesive than used commonly may be advantageously used. Such an adhesive could, for example, be as described in European patent application 97944750 or as used in so-called Eakin rings.

The invention claimed is:

1. A base plate for an ostomy appliance, the base plate comprising:
   an adhesive layer having a skin-facing side, configured to be attached to a skin surface of the user around a stoma, and an opposite backing side, the adhesive layer comprising a first adhesive and a second adhesive surrounding the first adhesive, the first adhesive includes swelling properties and the second adhesive is different from the first adhesive;
   a stoma-receiving hole extending through the first adhesive from the skin facing side to the backing side; and
   a backing layer secured to the backing side of the adhesive layer, with an aperture formed in the backing layer to have an aperture diameter that is smaller than a diameter of the stoma-receiving hole before the base plate is applied to a user, the aperture is located over the stoma-receiving hole of the adhesive layer to provide the base plate with a sealing flange that overlaps some but not all of the stoma-receiving hole, the sealing flange forming a circular, planar member substantially parallel to the skin facing side of the adhesive surface,
   wherein an inner periphery of the sealing flange is configured, when the skin-facing side of the adhesive layer is attached to the skin surface of the user around the stoma, to be distally deflected by peristomal skin projecting above the skin surface around the stoma of the user, such that a seal is created around the stoma by the attached adhesive layer and the deflected inner periphery of the sealing flange.

2. The base plate according to claim 1, wherein a radial extent of the first adhesive is between 4 and 10 mm.

3. The base plate according to claim 1, wherein the backing layer is an open-celled foam.

4. The base plate according to claim 1, wherein the backing layer is a visco-elastic polyurethane foam.

5. The base plate according to claim 1, wherein the sealing flange extends between 7 and 15 mm beyond the first adhesive.

6. The base plate according to claim 2, wherein the radial extent of the first adhesive is 5 mm.

7. The base plate according to claim 1, wherein the first adhesive is located at and around the stoma receiving hole.

8. The base plate according to claim 1, wherein sealing flange prevents the first adhesive from expanding beyond an edge of the backing layer.

9. The base plate according to claim 1, wherein the sealing flange is not covered by adhesive.

10. The base plate according to claim 1, wherein the sealing flange separates the first adhesive from a stoma and prevents the first adhesive from contracting stoma effluent.

11. The base plate according to claim 1, wherein the first adhesive is moisture permeable.

12. The base plate according to claim 1, wherein the first adhesive is selected from the group consisting of polypropyleneoxide, polyurethane, silicone, polyacrylate, ethylene vinyl acetate, and mixtures of polypropyleneoxide, polyurethane, silicone, polyacrylate, ethylene vinyl acetate.

13. The base plate according to claim 1, further including a coupling ring to which an ostomy bag may be coupled, the coupling ring disposed radially outward from the sealing flange and the stoma-receiving hole.

* * * * *